(12) United States Patent
Lee et al.

(10) Patent No.: US 8,822,551 B2
(45) Date of Patent: Sep. 2, 2014

(54) IMPLANTATION MATERIAL COMPRISING BIOCOMPATIBLE POLYMER

(71) Applicant: Genewel Co., Ltd, Gyeonggi-do (KR)

(72) Inventors: Young Woo Lee, Gyeonggi-do (KR); Wan Jin Cho, Gyeonggi-do (KR); Ji Yeon Jang, Gyeonggi-do (KR)

(73) Assignee: Genewel Co., Ltd., Gyeonggi-Do (KR)

( * ) Notice: Subject to any disclaimer, the term of this patent is extended or adjusted under 35 U.S.C. 154(b) by 0 days.

(21) Appl. No.: 13/848,841

(22) Filed: Mar. 22, 2013

(65) Prior Publication Data

US 2013/0253074 A1  Sep. 26, 2013

(30) Foreign Application Priority Data

Mar. 26, 2012 (KR) .................. 10-2012-0030540

(51) Int. Cl.
  *A61K 47/00* (2006.01)
  *C08B 37/00* (2006.01)
  *C07K 14/78* (2006.01)
  *C08H 1/00* (2006.01)
  *C08B 37/08* (2006.01)

(52) U.S. Cl.
  CPC ......... *C08B 37/0072* (2013.01); *C08B 37/0075* (2013.01); *C08B 37/0069* (2013.01); *C07K 14/78* (2013.01); *C08H 1/00* (2013.01); *C08B 37/0084* (2013.01)
  USPC ........................... 514/774; 514/777; 514/779

(58) Field of Classification Search
  USPC ........................................ 514/774, 777, 866
  See application file for complete search history.

(56) References Cited

U.S. PATENT DOCUMENTS

| 4,500,676 A | 2/1985 | Balazs et al. |
| 4,713,448 A | 12/1987 | Balazs et al. |
| 4,716,154 A | 12/1987 | Mälson |
| 4,716,224 A | 12/1987 | Sakurai et al. |
| 4,886,787 A | 12/1989 | de Belder et al. |
| 4,963,666 A | 10/1990 | Mälson |
| 5,827,937 A | 10/1998 | Ågerup |
| 6,703,444 B2 * | 3/2004 | Zhao et al. ............. 525/61 |

FOREIGN PATENT DOCUMENTS

| CN | 1342170 A | | 3/2002 |
| EP | 0 161 887 A2 | | 11/1985 |
| EP | 1 120 428 A2 | | 8/2001 |
| JP | H07-102002 | | 4/1995 |
| JP | 2002-536465 A | | 2/2000 |
| KR | 10-2007-0004159 | | 1/2007 |
| KR | 10-2009-0012439 | | 2/2009 |
| KR | 10-2010-0132878 | | 12/2010 |
| WO | WO 00/46252 | | 8/2000 |
| WO | WO 2005/032417 | * | 4/2005 |
| WO | WO 2010/061005 | * | 6/2010 |

OTHER PUBLICATIONS

Tomihata et al (Biomaterials (1997) 189-195.*
Balazs et al. (1986)"Nomenclature of hyaluronic acid" Biochemical Journal, 235, 903.
Adams, M.E., (1998) "Viscosupplementation as articular therapy," in The Chemistry, Biology and Medical Applications of Hyaluronan and Its Derivatives, T.C. Laurent (ed.), Portland Press, London, pp. 243-253.
Luciano et al. (1983) "Evaluation of commonly used adjuvants in the prevention of postoperative adhesions", Am. J. Obstet. Gynecol., 146, 88-92.
Meyers et al. (1934) "The Polysaccharide of the Vitreous Humor" Journal of Biology and Chemistry 107: 629-634.
Schmitz et al. (1986) "The Critical Size Defect as an Experimental model for Craniomandibulofacial Nonunions" Clin. Orthop. Relat. Res., 205, 299-308.
Toole et al. (1997) "Hyaluronan in morphogenesis" Journal of Internal Medicine, 242:35-40.
European Search Report for EP 13161184.0 mailed Jul. 19, 2013, 7 pages.
Tomihata and Ikada (1997) Biomaterials 18:189-195 "Preparation of cross-linked hyaluronic acid films of low water content".

* cited by examiner

*Primary Examiner* — Shirley V Gembeh
(74) *Attorney, Agent, or Firm* — Swanson & Bratschun, L.L.C.

(57) ABSTRACT

Disclosed herein is a hyaluronic acid epoxide derivative film comprises a polymer containing a hydroxyl (—OH) terminal group. The film is prepared by allowing an epoxy crosslinker to react with a mixture of hyaluronic acid and a polymer containing a hydroxyl (—OH) terminal group and has improved physical strength, in vivo stability, flexibility, adhesiveness to biological tissue, and biocompatibility.

7 Claims, 7 Drawing Sheets

| | experimental group 1 | experimental group 2 | experimental group 3 |
|---|---|---|---|
| 2 weeks |  |  |  |
| 4 weeks | N/D |  |  |
| 12 weeks | N/D |  |  |

IMPLANTATION MATERIAL COMPRISING BIOCOMPATIBLE POLYMER

CROSS-REFERENCE TO RELATED APPLICATIONS

The present invention claims the benefit of Korean Patent Application No. 10-2012-0030540, filed on Mar. 26, 2012.

RELATED APPLICATIONS

This application claim prior to Korean patent application serial no. 10-2012-0030540, filed Mar. 26, 2012.

BACKGROUND OF THE INVENTION

1. Field of the Invention

The present invention relates to a hyaluronic acid epoxide derivative film, and more particularly to a hyaluronic acid epoxide derivative film which is prepared by allowing an epoxide crosslinker to react with a mixture of hyaluronic acid and a polymer containing a hydroxyl (—OH) terminal group and has improved physical strength, in vivo stability, flexibility, adhesiveness to biological tissue, and biocompatibility.

2. Description of the Prior Art

Hyaluronic acid which was first isolated from vitreous humor by Meyer and Palmer in 1934 is a polyanionic mucopolysaccharide and is a biopolymer that is widely found in nature (Meyer K. et al., *Journal of Biology and Chemistry* 107 629-34 (1934)). Hyaluronic acid is abundantly found in animal placentae, eyes, and connective tissues such as joints, and is also produced in *Streptococcus* sp. microorganisms, *Streptococcus equi, Streptococcus zooepidemicus* and the like. It has a structure in which repeating units of glucuronic acid and N-acetylglucosamine, which are linked by $\beta(1,3)$ glycosidic bonds, are continuously linked to each other by $\beta(1,4)$ glycosidic bonds to form a long chain structure (Balazs E. A. et al., *Biochemical Journal*, 235, 903, 1986; Toole B. P. et al., *Journal of Internal Medicine*, 242, 35-40 (1997)).

Hyaluronic acid has excellent biocompatibility and is highly viscoelastic in a solution state. Thanks to such properties, hyaluronic acid is widely used not only in cosmetic applications, including cosmetic additives, but also in various pharmaceutical applications, including ophthalmic surgical aids, joint function-improving agents, drug delivery materials, and eyedrops. However, because hyaluronic acid is easily degraded in vivo or under acidic or alkaline conditions, the use thereof is limited. Thus, there have been many efforts to develop structurally stable hyaluronic acid derivatives (Laurent T. C. et al., Portland Press Ltd., London, 1998).

Hyaluronic acid derivatives have excellent biocompatibility, physical stability and biodegradability, and thus have been developed for use in various applications, including implants for plastic surgery, joint function-improving agents, drug delivery materials, cell culture scaffolds, and materials for preventing post-surgical adhesion.

Among methods for obtaining hyaluronic acid derivatives, methods employing epoxide crosslinkers have been developed to provide products in various forms, including solutions, gels, fibers, sponges and films. Methods for producing these products are disclosed in U.S. Pat. Nos. 4,500,676, 4,713,448, 4,716,224, 4,716,154, 4,886,787, 4,963,666, 5,827,937, etc.

However, the hyaluronic acid epoxide derivative films have problems in that shrinkage occurs during drying, making it difficult to produce uniform films, and in that the physical strength of the films is reduced during purification.

In an attempt to overcome these problems occurring in the production of the hyaluronic acid epoxide derivative films, Korean Patent Laid-Open Publication No. 2009-0012439 discloses a film having improved flexibility and physical strength, which is produced by surface crosslinking of hyaluronic acid (HA) and carboxymethylcellulose (CMC). However, if the content of HA is increased, the film will have low physical strength, and thus will be rolled up in a wet state, and if the content of CMC is increased, the film will have a slow biodegradation rate so that it will remain for a time longer than required, thus causing foreign body reactions.

SUMMARY OF THE INVENTION

Accordingly, the present invention has been made in view of the problems occurring in the prior art, and it is an object of the present invention to provide a hyaluronic acid epoxide derivative film having a uniform shape and excellent physical strength, which does not comprise a CMC derivative moiety and is prepared while avoiding the problems occurring during the drying and purification of the hyaluronic acid derivative.

The hyaluronic acid epoxide derivative film of the present invention is characterized by excellent physical strength, in vivo stability, flexibility, adhesiveness to biological tissue, and biocompatibility.

The above and other objects of the present invention may be accomplished by the present invention as described below.

The present invention has been made in order to solve the problems occurring in the prior art and provides a hyaluronic acid epoxide derivative film having a uniform shape and excellent physical strength, in vivo stability, flexibility, adhesiveness to biological tissue, and biocompatibility, which is prepared using a polymer comprising a hydroxyl terminal group to prevent shrinkage and a decrease in physical strength from occurring during the drying and purification of the hyaluronic acid derivative.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE INVENTION

The present invention provides a hyaluronic acid epoxide derivative film comprising a polymer containing a hydroxyl (—OH) terminal group.

Hereinafter, the present invention will be described in detail.

Figure 1:
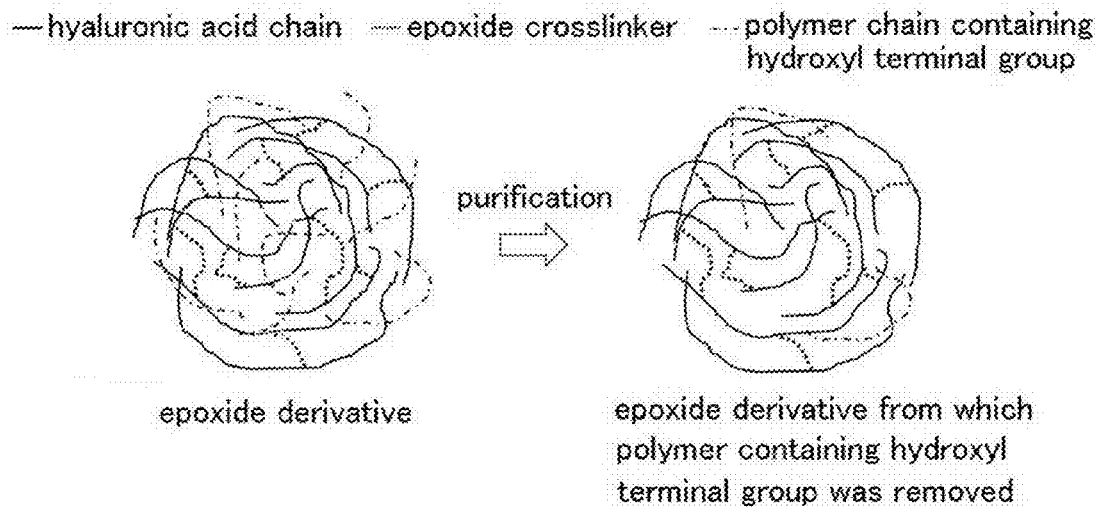
FIG. 1 is a schematic view showing a structure in which a polymer containing a hydroxyl terminal group is physically bonded to crosslinked hyaluronic acid according to one embodiment of the present invention, and a structure which remains after purification and from which the polymer containing the hydroxyl terminal group was mostly removed.

Specifically, in the present invention, hyaluronic acid and a polymer containing a hydroxyl terminal group are mixed with each other, and the hyaluronic acid is crosslinked with an epoxide crosslinker having at least two epoxide groups. As shown in FIG. 1, the polymer containing the hydroxyl terminal group serves to prevent shrinkage during solidification into a film and is slowly removed during purification while it prevents the shape of the hyaluronic acid derivative film from being changed.

Figure 6:
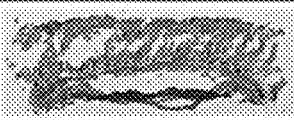
FIG. 6 is a set of photographs showing the results of tissue staining carried out to determine the in vivo residence time of hyaluronic acid derivative films in Test Example 5 of the present invention.
Figure 6:
Figure 6:
Figure 6:
Figure 6:
Figure 6:
Figure 6:

In addition, after the hyaluronic acid epoxide derivative has been purified, it may be precipitated in an organic solvent to improve the physical strength that was reduced during the purification process (see FIG. 6).

The hyaluronic acid epoxide derivative film is comprised of 50-90 wt % of the hyaluronic acid and 10-50 wt % of the polymer containing the hydroxyl terminal group.

The hyaluronic acid derivative film may have a crosslinking density of 1-100 mole %, preferably 5-50 mole %. If the crosslinking density is less than 1 mole %, a change in the shape of the film will occur due to its high water absorption ability and it will be difficult to purify the derivative, and if the crosslinking density is more than 100 mole %, the film will be easily broken and a large amount of the crosslinker will remain in the film.

In the present invention, the hyaluronic acid epoxide derivative can be prepared by allowing an epoxide crosslinker to react with hyaluronic acid or hyaluronate alone or in combination with a polymer capable forming an ether covalent bond with hyaluronic acid.

Herein, the hyaluronate may be one or more selected from the group consisting of sodium hyaluronate, potassium hyaluronate, calcium hyaluronate, magnesium hyaluronate, zinc hyaluronate, cobalt hyaluronate, and tetrabutylammonium hyaluronate. Among them, sodium hyaluronate is preferably used, but is not limited thereto.

In the present invention, the polymer capable of forming an ether covalent bond with hyaluronic acid may be one or more selected from the group consisting of hyaluronic acid, collagen, alginic acid, heparin, gelatin, elastin, fibrin, laminin, fibronectin, proteoglycan, heparan sulfate, chondroitin sulfate, dermatan sulfate, and keratin sulfate.

In the present invention, the polymer containing the hydroxyl terminal group may be one or more selected from the group consisting of polyethylene oxide, polyvinyl alcohol, polypropylene oxide, a polyethylene oxide-polypropylene oxide copolymer, a polyethylene oxide-polylactic acid copolymer, a polyethylene oxide-polylactic glycolic acid copolymer, a polyethylene oxide-polycaprolactone copolymer, polybutylene oxide, polyoxyethylene alkyl ethers, polyoxyethylene castor oil derivatives, polyoxyethylene sorbitan fatty acid esters, and polyoxyethylene stearates.

A process of preparing the hyaluronic acid derivative using the epoxide crosslinker according to the present invention is shown in the following reaction scheme 1:

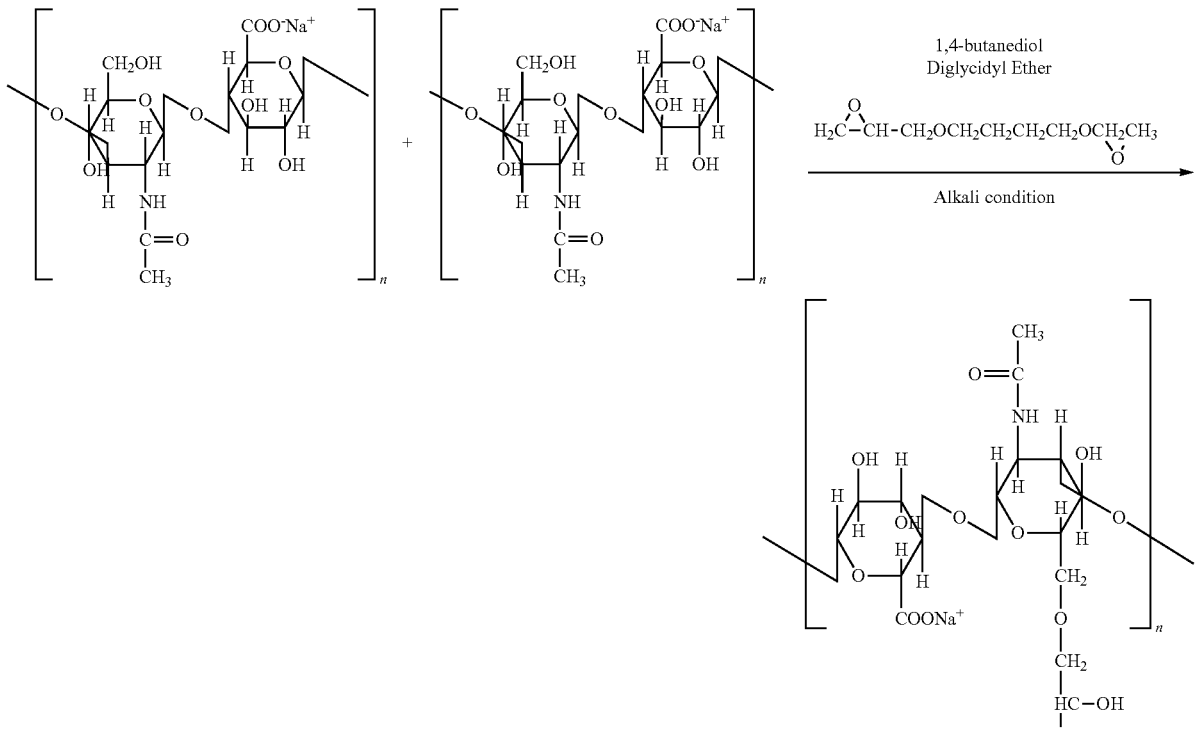

Reaction Scheme 1

-continued

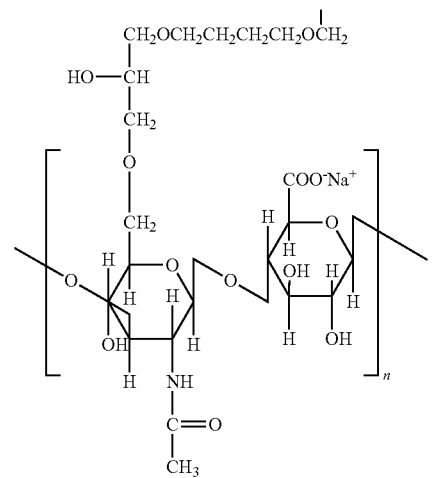

The epoxide crosslinker that is used in the present invention is one or more selected from the group consisting of polyethylene glycol diglycidyl ether, 1,4-butanediol diglycidyl ether, ethylene glycol diglycidyl ether, 1,6-hexanediol diglycidyl ether, propylene glycol diglycidyl ether, poly(propylene glycol)diglycidyl ether), poly(tetramethylene glycol) diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene), pentaerythritol polyglycidyl ether, and sorbitol polyglycidyl ether.

The crosslinker containing at least two epoxy functional groups serves to react with the hydroxyl (—OH) terminal groups to form an ether bond that crosslinks the hyaluronic acid.

The epoxide crosslinker may be used in an amount of 1-100 parts by weight, and preferably 5-50 parts by weight, based on 100 parts by weight of repeating units of the hyaluronic acid. If the crosslinker is used in an amount of less than 5 parts by weight, the resulting film will be deformed due to its high water absorption ability and will be difficult to purify, and if the crosslinker is used in an amount of more than 50 parts by weight, the film will be easily broken and a large amount of the crosslinker will remain in the film.

The organic solvent that is used to improve the physical strength of the hyaluronic acid epoxide derivative film in the present invention may be dimethyl sulfoxide (DMSO), dimethylformamide (DMF), acetonitrile, tetrahydrofuran (THF), acetone, an aqueous acetone solution, a $C_1$-$C_6$ alcohol such as methanol or ethanol, or an aqueous alcohol solution.

The hyaluronic acid epoxide derivative may be dried in a hydrated state to prepare a film, a membrane, sponge, or powder.

The hyaluronic acid epoxide derivative film according to the present invention has a high ability to absorb water, and thus can promote hemostasis and wound healing by absorbing exudates and blood from the wound.

In addition, the hyaluronic acid epoxide derivative film has high physical strength (see FIG. 4), and thus is easy to operate and can protect an affected part from the surrounding tissues.

Further, because it is stable to enzymes, it will form a physical barrier for a given time, and then will be completely degraded and absorbed in vivo (see FIG. 6).

Thanks to these properties, the hyaluronic acid epoxide derivative film may be used as a tissue repair material, a guided bone regeneration membrane or an adhesion barrier, but is not limited thereto.

Moreover, the guided bone regeneration membrane or adhesion barrier of the present invention may further comprise an antibacterial or anti-inflammatory natural substance which may be an extract of green tea, turmeric, black bean seed coats, rose flower leaves, *Paeonia radix, Platydodon grandiflorum* roots, bean sprouts, colored barley seed coats, camellia flowers, buckwheat, grapefruits, licorice, *Coptis chinensis, Astragalus membranaceus, Phellodendron amurense, Scutellaria baicalensis*, cinnamon, wood vinegar, *Rubus coreanus, Galla rhois, Juniperus chinensis, Forsythia, Capsicum annuum* leaves, *Mentha arvensis, Duchesnea chrysanthe*, mulberry, *Saururus chinensis*, pine, *Artemisia capillaries, Houttuynia cordata, Prunus yedoensis*, or *Sasa borealis*.

Hereinafter, the present invention will be described in detail with reference to examples. However, these examples are for illustrative purposes, and those skilled in the art will appreciate that various modifications, additions and substitutions are possible, without departing from the scope and spirit of the invention as disclosed in the accompanying claims.

EXAMPLES

Examples 1 to 4

Formation of Crosslinks in Polymers Which can be Used in a Mixture with Hyaluronic Acid In Examples 1 to 4, in order to determine whether polymers which can be used in a mixture with hyaluronic acid are crosslinked to form an ether covalent bond, 1 wt % of each of hyaluronic acid, alginic acid, gelatin and collagen was mixed with a 1 wt % hyaluronic acid solution at a ratio of 50:50, and 5 wt % of polyethylene oxide was added thereto. Then, each of epoxide crosslinkers (1,4-butanediol diglycidyl ether, polyethylene glycol diglycidyl ether, polypropylene diglycidyl ether, and neopentyl diglycidyl ether) was added to each of the mixtures in an amount of 5 parts by weight based on 100 parts by weight of repeating units of the polymer mixture. Then, each of the mixture was subjected to a crosslinking reaction at room temperature for 12 hours, and the formed solid materials were stored in deionized water for 1 hour. Whether the solid materials were dissolved in deionized water was examined to determine whether crosslinks were formed.

TABLE 1

| Examples | Polymers | Crosslinkers | Dissolved or not dissolved |
|---|---|---|---|
| Example 1 | Hyaluronic acid | 1,4-butanediol diglycidyl ether | Not dissolved |
| | | Polyethylene glycol diglycidyl ether | Not dissolved |
| | | Polypropylene glycol diglycidyl ether | Not dissolved |
| | | Neopentyl diglycidyl ether | Not dissolved |
| Example 2 | Alginic acid | 1,4-butanediol diglycidyl ether | Not dissolved |
| | | Polyethylene glycol diglycidyl ether | Not dissolved |
| | | Polypropylene glycol diglycidyl ether | Not dissolved |
| | | Neopentyl diglycidyl ether | Not dissolved |
| Example 3 | Gelatin | 1,4-butanediol diglycidyl ether | Not dissolved |
| | | Polyethylene glycol diglycidyl ether | Not dissolved |
| | | Polypropylene glycol diglycidyl ether | Not dissolved |
| | | Neopentyl diglycidyl ether | Not dissolved |
| Example 4 | Collagen | 1,4-butanediol diglycidyl ether | Not dissolved |
| | | Polyethylene glycol diglycidyl ether | Not dissolved |
| | | Polypropylene glycol diglycidyl ether | Not dissolved |
| | | Neopentyl diglycidyl ether | Not dissolved |

As can be seen in Table 1 above, the solid materials prepared by mixing each of hyaluronic acid, alginic acid, gelatin and collagen with each of the epoxide crosslinker were swollen without being dissolved in deionized water. These results suggest that, when hyaluronic acid, alginic acid, gelatin or collagen is mixed with the epoxide crosslinker, an ether covalent bond is formed therein so that the polymer is stably present in deionized water.

Example 5

Preparation of a Hyaluronic Acid Epoxide Derivative Film Comprising a Polymer Containing a Hydroxyl Terminal Group In this Example, propylene oxide was used as a polymer containing a hydroxyl terminal group. A solution obtained by mixing 10 wt % of hyaluronic acid with 30 wt % of propylene oxide in 0.25N NaOH was placed in each of three reactors. Polyethylene diglycidyl ether was added to the solution in each reactor in amounts of 5, 10 and 25 parts by weight based on 100 parts by weight of the hyaluronic acid of each solution. Each of the mixtures was allowed to react at room temperature for 24 hours, and each of the reaction products was uniformly spread in a rectangular dish, and then dried at room temperature for 12 hours, thereby preparing primary films. The primary films were washed with purified water to remove unreacted materials and polypropylene oxide, and then precipitated in ethanol and shrunk, thereby preparing secondary films. The secondary films swollen in purified water and dried, thereby preparing final derivative films. The derivative films prepared for use in the Test Examples of the present invention were named "experimental group 1" (5 parts by weight), "experimental group 2" (10 parts by weight), and "experimental group 3" (25 parts by weight) according to the amount of crosslinker used.

Comparative Example 1

Preparation of a Hyaluronic Acid Epoxide Derivative Film which does not Comprise a Polymer Containing a Hydroxyl Terminal Group 10 wt % of hyaluronic acid was dissolved in 0.25N NaOH to prepare a hyaluronic acid solution. Polyethylene glycol diglycidyl ether was added to the solution in an amount of 25 parts by weight based on 100 parts by weight of the hyaluronic acid, and the mixture was allowed to react at room temperature for 24 hours. The reaction solution was spread uniformly in a rectangular dish and dried at room temperature at room temperature for 12 hours to prepare a primary film which was then washed with purified water to remove unreacted materials. The resulting hydrated derivative was precipitated in ethanol and shrunk to prepare a secondary film which was then swollen in purified water and dried, thereby preparing a final derivative film. The derivative film prepared in Comparative Example 1 was named "experimental group 4".

TEST EXAMPLES

Test Example 1

Comparison of Shape Between a Film Comprising a Hydroxyl Terminal Group-Containing Polymer and a Film Comprising No Hydroxyl Terminal Group-Containing Polymer In order to examine the uniformity of the film comprising the hydroxyl terminal group-containing polymer, the shape of the primary film prepared in Example 5 and Comparative Example 1 were compared with each other by photographs.

Figure 2:
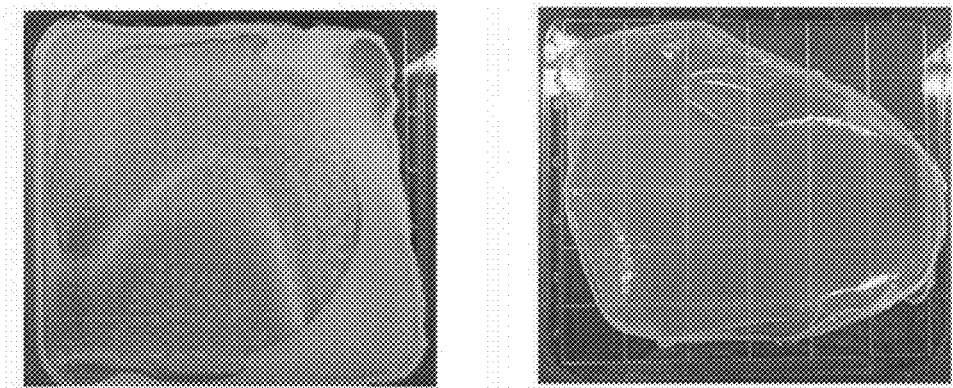
FIG. 2 is a set of photographs obtained in Test Example 1 of the present invention and showing a comparison of shape between a film comprising a hydroxyl terminal group-containing polymer and a film which does not comprises the hydroxyl terminal group-containing polymer.

As shown in FIG. 2, the film comprising no hydroxyl terminal group-containing polymer was significantly shrunk and rolled up after drying, whereas the film comprising the hydroxyl terminal group-containing polymer was slightly shrunk at the edge, but was not rolled up. These results suggest that the hydroxyl terminal group-containing polymer functions to prevent shrinkage during the process in which the solution is solidified into the film.

Test Example 2

Analysis of Structure of Hyaluronic Acid Epoxide Derivative Film 1 wt % of hyaluronic acid was dissolved in deionized water to prepare a hyaluronic acid solution, and 10 wt % of a polymer containing a hydroxyl terminal group was dissolved in deionized water to prepare a solution. Each of the prepared solutions was placed in a rectangular dish and dried at room temperature for 12 hours, thereby preparing a hyaluronic acid film and a hydroxyl terminal group-containing polymer film. The structures of the hyaluronic acid film, the hydroxyl terminal group-containing polymer film, experimental group 3 and experimental group 4 were analyzed by ATR-IR.

Figure 3:
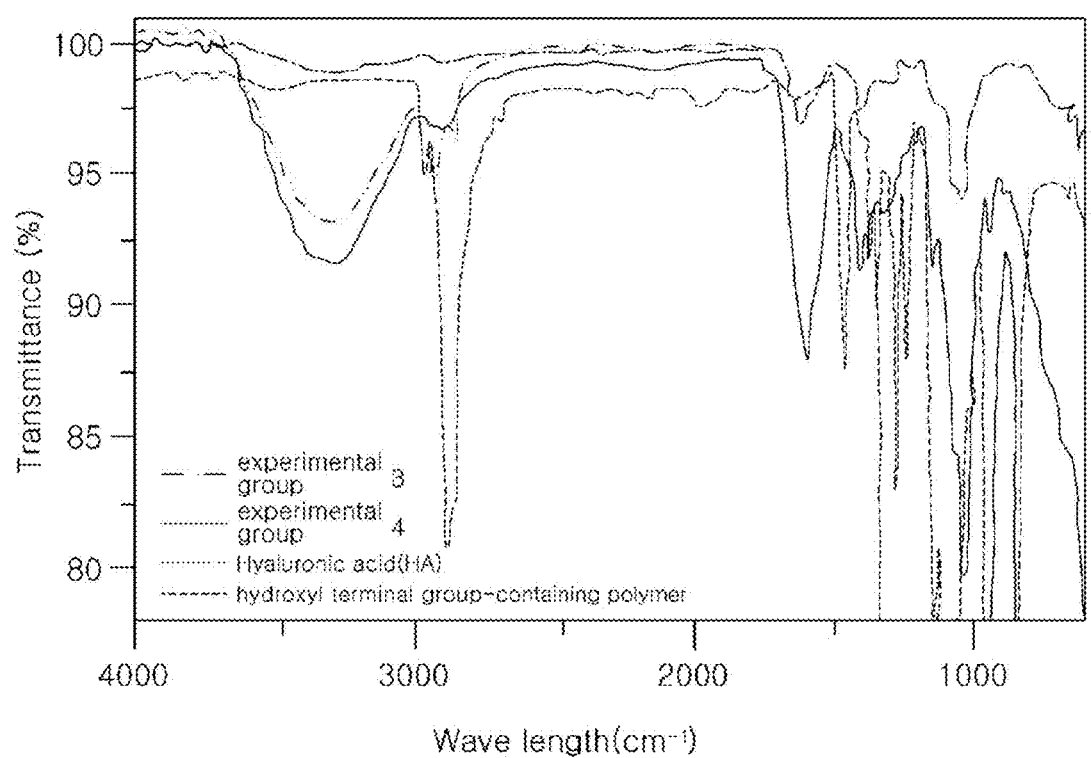
FIG. 3 shows the IR spectrum of a hyaluronic acid epoxide derivative film comprising a hydroxyl terminal group-containing polymer, measured in Test Example 2 of the present invention.

FIG. 3 shows the IR spectra of the films. As can be seen therein, the hydroxyl terminal group-containing polymer film showed a strong peak at 2885 $cm^{-1}$ (C—H, methylene), and similar thereto, experimental group 3 comprising the hydroxyl terminal group-containing polymer also showed a strong peak at 2925 $cm^{-1}$, suggesting that hyaluronic acid was mixed with the hydroxyl terminal group-containing polymer. These results reveal that, in the case of the hyaluronic acid derivative comprising the hydroxyl terminal group-containing polymer, a specific amount of the hydroxyl terminal group-containing polymer remains even after purification.

Test Example 3

Measurement of Physical Strength of Hyaluronic Acid Derivative Epoxide Derivative The physical strengths of experimental groups 1, 2 and 3 in Example 5, the commercially available adhesion barrier Interceed (J&J, USA) as a comparison group 1, and the guided bone regeneration membrane Bio-Gide (Geistlich Pharma AG, Switzerland) as a comparison group 2 was comparatively measured. For measurement, each of the samples was cut into a size of 3 cm×1 cm and placed in the grip of a universal material tester (Instron, USA), and then the force applied to each of the samples was measured at a pulling speed of 10 mm/min.

Figure 4:
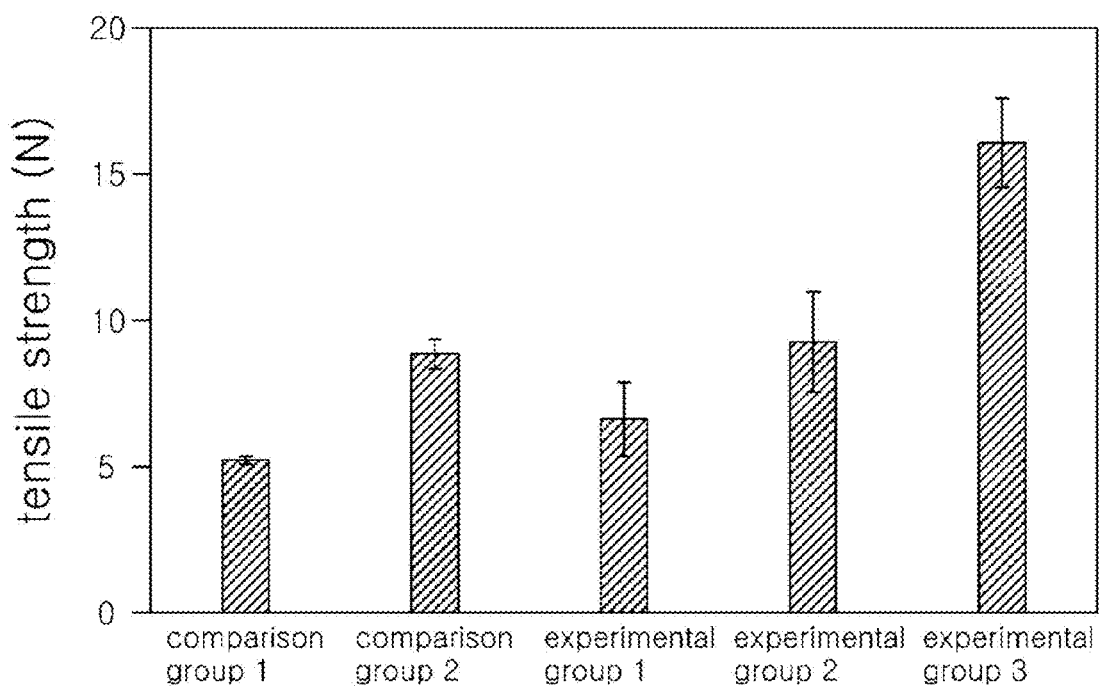
FIG. 4 shows a comparison of tensile strength between hyaluronic acid epoxide derivative films (experimental groups 1, 2 and 3), the commercially available adhesion barrier Interceed (comparison group 1) and the Guided bone regeneration membrane Bio-Gide (comparison group 2), carried out in Test Example 4 of the present invention.

FIG. 4 shows a comparison of tensile strength (N) between the experimental groups and the comparison groups. As can be seen therein, as the content of the crosslinker increased, the physical strength increased, and all the experimental groups showed higher tensile strengths than comparison group 1 (Interceed). However, experimental group 1 showed a slightly lower tensile strength compared to comparison group 2 (Bio-Gide), but this difference was not statistically significant.

These results suggest that the hyaluronic acid derivative film has suitable physical strength so that it may be used as an adhesion barrier or a guided bone regeneration membrane.

Test Example 4

Comparison Between Physical Strength Between Film Treated with Organic Solvent and Film not Treated with Organic Solvent In order to compare the physical strength of the film, obtained by treating the hydrated hyaluronic acid (HA) with ethanol in Example 5, with that of the film not treated with ethanol, samples were prepared in the same manner as Example 5, except that the hydrated HA derivatives were not precipitated in ethanol. The physical strength of each of the samples prepared as described in Example 5 was measured.

Figure 5:
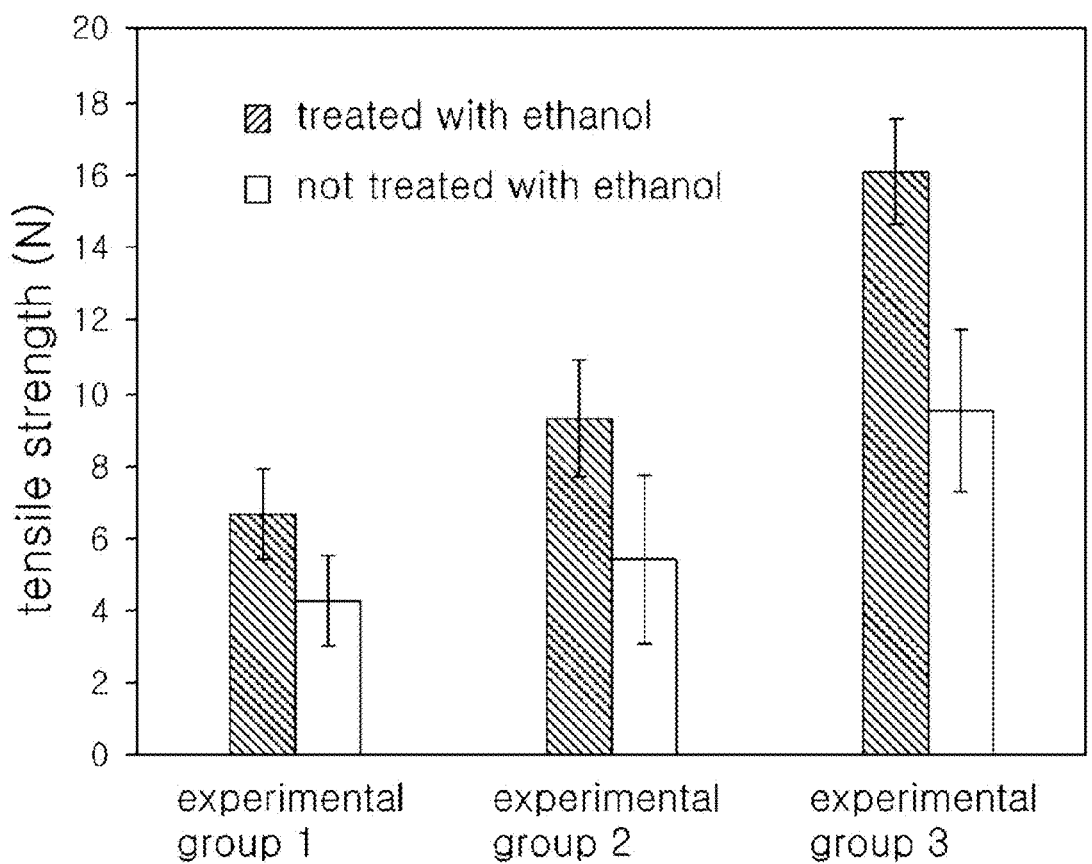
FIG. 5 shows a comparison of tensile strength between a hyaluronic acid epoxide derivative film treated with an organic solvent and a hyaluronic acid epoxide derivative film not treated with an organic solvent, carried out in Test Example 4 of the present invention.

As can be seen in FIG. 5, the samples treated with ethanol showed higher physical strengths than samples not treated with ethanol. These results indicate that the process of treating the hyaluronic acid derivative with an organic solvent such as ethanol increases the physical strength of the hyaluronic acid derivative.

Test Example 5

Evaluation of in vivo Residence Time of Hyaluronic Acid Derivative Film

In order to evaluate the in vivo residence time of the samples prepared in Example 5, an animal test was performed using 8-week-old SD rats. Specifically, the rats were anesthetized by injecting an anesthetic into the lower abdominal region of the rats, and each sample having a size of 5 mm×10 mm was implanted into the back portion of each rat. At 2, 4 and 12 weeks after implantation, histological analysis (H & E staining) was performed to evaluate whether the sample remained.

FIG. 6 shows the results of the histological analysis. As can be seen therein, experimental group 1 was detected in vivo up to 2 weeks, but was not detected at 4 and 12 weeks. These results suggest that the in vivo residence time of the hyaluronic acid epoxide derivative film changes depending on the content of the crosslinker, but the hyaluronic acid epoxide derivative is stably maintained in vivo for a specific time without being easily degraded.

Test Example 6

Evaluation of Anti-Adhesion Effect of Hyaluronic Acid Epoxide Derivative Film The anti-adhesion effect of the samples prepared in Example 5 was evaluated using animal models (SD rats). Specifically, the rats were anesthetized by injecting an anesthetic into the lower abdominal region of the rats. The abdomen of each of the anesthetized rats was incised, and a wound having a size of 1 cm×2 cm was formed in the epidermal portion of the peritoneum using a bone burr, and the cecum coming in contact with the wound was wounded such that the epidermis was slightly peeled off. Tissue adhesion was compared between a control group in which no adhesion barrier was used between the wounds, comparison group 1 (Interceed), and experimental groups 1, 2 and 3 prepared in Example 5. Each of the samples was cut into a size of 2 cm×3 cm before use. The degree of tissue adhesion was evaluated based on a 4-grade scale (0, 1, 2 and 3; greater values indicate more severe adhesion) using an adhesion grading system (A. A. Luciano, et al., "Evaluation of commonly used adjuvants in the prevention of postoperative adhesions", *Am. J. Obstet. Gynecol.*, 146, 88-92 (1983)).

In addition, for the animals in which tissue adhesion occurred, the strength of adhesion was evaluated based on a 3-grade scale (1, 2 and 3; greater values indicate stronger adhesion strengths).

Figure 7:
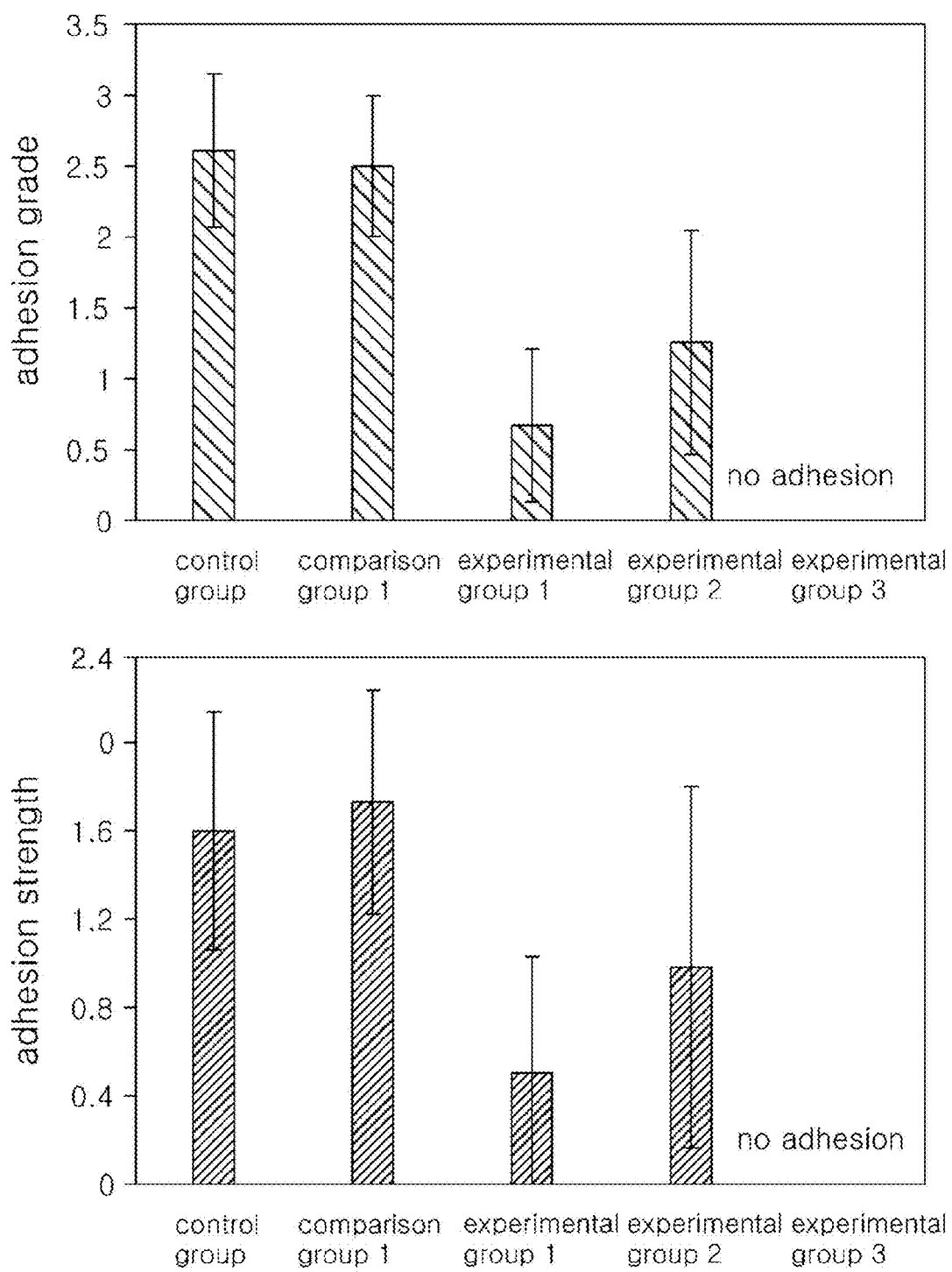
FIG. 7 is a set of graphs showing adhesion grade and adhesion strength in three experimental groups treated with hyaluronic acid epoxide derivative films of the present invention, a comparison group 1 treated with the commercially available adhesion barrier Interceed, and a control group not treated with an anti-adhesion agent, measured to evaluate anti-adhesion performance in Test Example 6 of the present invention.

FIG. 7 shows the results of evaluation of tissue adhesion and adhesion intensity, obtained in the animal test. As can be seen therein, the degrees of tissue adhesion in experimental groups 1. 2 and 3 were 0.67±0.82, 1.25±0.96, and 0, respectively, which were lower than 2.6±0.54 for the control group and 2.5±0.58 for comparison group. In addition, the adhesion intensities in experimental groups 1, 2 and 3 were 0.5±0.54, 1±0.8 and 0, respectively, which were lower than 1.6±0.54 for the control group and 1.75±0.5 for comparison group 1.

The results of the anti-adhesion effect test indicate that the anti-adhesion effect of the hyaluronic acid epoxide derivative film of the present invention slightly changed depending on the content of the crosslinker, but the film of the present invention showed lower adhesion severity compared to the control group and comparison group 1, suggesting that it is effective in preventing tissue adhesion.

Test Example 7

Evaluation of Degree of Bone Regeneration Resulting from Hyaluronic Acid Epoxide Derivative Film In order to examine the bond regeneration effect of experimental group 3 prepared in Example 5, 8-week-old SD rats were used as animal models. The animals were anesthetized, and then the skin of the center of the brow was incised by about 4 cm, after which the periosteum was incised, and in this state, a defect area having a diameter of 8 mm (critical size defect) was formed such that blood vessels passing through dura mater and the cranial midline were not damaged (J. P Schmitz et al., *Clin. Orthop. Relat. Res.*, 205, 299 (1986)). Then, each of experimental group 3 and comparison group 2 was cut into a circular shape having a size of Φ 12 mm, and the defect area was covered with each of the cut samples, and the periosteum and the skin were sutured. In addition, the control group in which the bone defect area was not treated with anything was also tested. After the animals have been raised for 12 weeks, the animals were sacrificed, and the bone defect area was collected from the animals and analyzed by micro-CT and soft X-rays to evaluate the bone regeneration effects of the samples.

Figure 8:
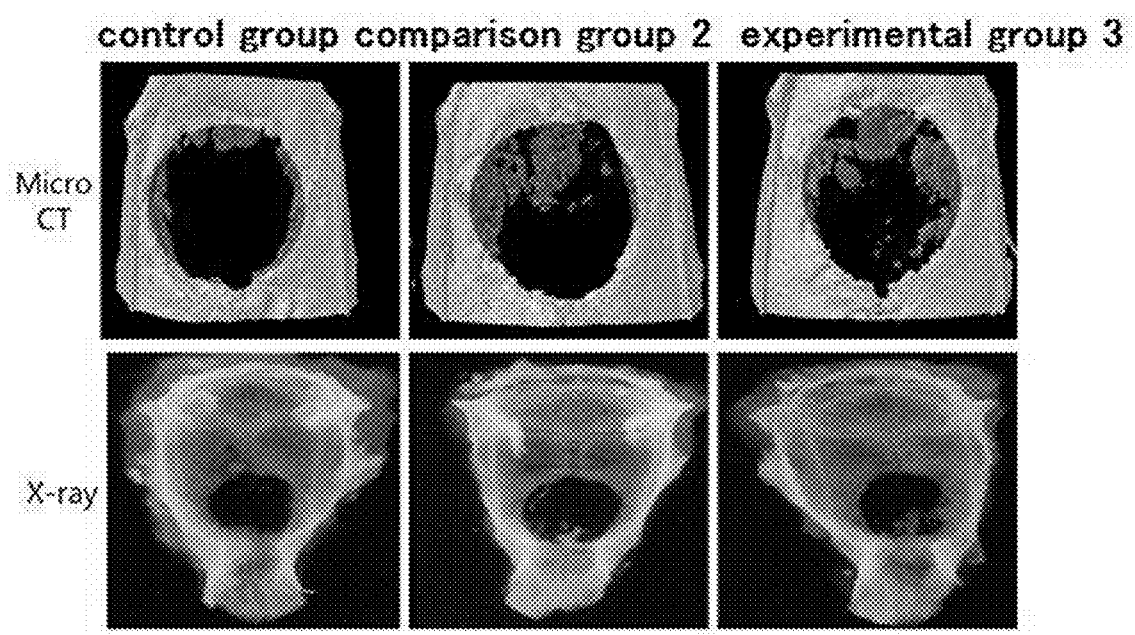
FIG. 8 is a set of photographs showing the degree of bone regeneration in experimental group 3 treated with a hyaluronic acid epoxide film of the present invention, comparison group 2 treated with the guided bone regeneration membrane Bio-Gide, and a control group whose bone defect was not treated with anything, measured in Test Example 7 of the present invention.

The results of the analysis are shown in FIG. 8. As can be seen therein, the bone regeneration effect of experimental group 1 was superior to that of the control group and equal to that of the commercially available guided bone regeneration membrane Bio-Gide (comparison group 2). These results indicate that the hyaluronic acid epoxide derivative film has excellent ability to regenerate bone.

As described above, the present invention provides the hyaluronic acid epoxide derivative film having improved uniformity, physical strength, in vivo stability, flexibility, adhesion to biological tissue, and biocompatibility.

In addition, the hyaluronic acid epoxide derivative film of the present invention has excellent biocompatibility, biodegradability, physical stability and the like, and thus can be used in various applications, including wound dressings, cell scaffolds, drug delivery materials, guided bone regeneration membrane, and adhesion barrier.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A hyaluronic acid epoxide derivative film, wherein a polymer containing a hydroxyl (—OH) terminal group is physically bonded to a crosslinked hyaluronic acid structure; wherein the hyaluronic acid epoxide derivative film is comprised of 50-90 wt % of hyaluronic acid and 10-50 wt % of the polymer containing the hydroxyl (—OH) terminal group;

wherein the polymer containing the hydroxyl (—OH) terminal group is one or more selected from the group consisting of polyethylene oxide, polyvinyl alcohol, polypropylene oxide, a polyethylene oxide-polypropylene oxide copolymer, a polyethylene oxide-polylactic acid copolymer, a polyethylene oxide-polylactic glycolic acid copolymer, a polyethylene oxide-polycaprolactone copolymer, polybutylene oxide, polyoxyethylene alkyl ethers, polyoxyethylene castor oil derivatives, polyoxyethylene sorbitan fatty acid esters, and polyoxyethylene stearates;

wherein the crosslinked hyaluronic acid structure is formed by reacting 100 parts by weight of hyaluronic acid, hyaluronic acid salt or a mixture thereof, and 5-25 parts by weight of an epoxide crosslinker under basic conditions; and wherein the derivative film has a crosslinking density of 1-100 mole %.

2. The hyaluronic acid epoxide derivative film of claim 1, wherein the hyaluronate is one or more selected from the group consisting of sodium hyaluronate, potassium hyaluronate, calcium hyaluronate, magnesium hyaluronate, zinc hyaluronate, cobalt hyaluronate, and tetrabutylammonium hyaluronate.

3. The hyaluronic acid epoxide derivative film of claim 1, wherein the hyaluronic acid further comprises a polymer capable of forming the ether covalent bond selected from the group consisting of hyaluronic acid, collagen, alginic acid, heparin, gelatin, elastin, fibrin, laminin, fibronectin, proteoglycan, heparan sulfate, chondroitin sulfate, dermatan sulfate, and keratin sulfate.

4. The hyaluronic acid epoxide derivative film of claim 1, wherein the epoxide crosslinker is one or more selected from the group consisting of polyethylene glycol diglycidyl ether, 1,4-butanediol diglycidyl ether, ethylene glycol diglycidyl ether, 1,6-hexanediol diglycidyl ether, propylene glycol diglycidyl ether, poly(propylene glycol)diglycidyl ether), poly(tetramethylene glycol)diglycidyl ether, neopentyl glycol diglycidyl ether, polyglycerol polyglycidyl ether, diglycerol polyglycidyl ether, glycerol polyglycidyl ether, trimethylpropane polyglycidyl ether, 1,2-(bis(2,3-epoxypropoxy)ethylene), pentaerythritol polyglycidyl ether, and sorbitol polyglycidyl ether.

5. The hyaluronic acid epoxide derivative film of claim 1, wherein the derivative film is prepared by precipitation in an organic solvent selected from the group consisting of dimethyl sulfoxide, dimethylformamide, acetonitrile, tetrahydrofuran, acetone, an aqueous acetone solution, a C1-C6 alcohol or an aqueous C1-C6 alcohol solution, after purification of the hyaluronic acid epoxide derivative.

6. The hyaluronic acid epoxide derivative film of claim 1, wherein the derivative film is used as an adhesion barrier or a guided bone regeneration membrane.

7. The hyaluronic acid epoxide derivative film of claim 6, wherein the derivative film further comprises an antibacterial and anti-inflammatory natural substance.

* * * * *